(12) United States Patent
Scott et al.

(10) Patent No.: US 9,265,853 B2
(45) Date of Patent: Feb. 23, 2016

(54) FRAGRANCE DISPENSING DEVICES AND METHODS

(75) Inventors: J. Henry Scott, Warren, NJ (US); Michael Gordon, Warren, NJ (US)

(73) Assignee: Innovaci Inc., Basking Ridge, NJ (US)

(*) Notice: Subject to any disclaimer, the term of this patent is extended or adjusted under 35 U.S.C. 154(b) by 824 days.

(21) Appl. No.: 13/537,768

(22) Filed: Jun. 29, 2012

(65) Prior Publication Data

US 2014/0001286 A1  Jan. 2, 2014

(51) Int. Cl.
*A24F 25/00* (2006.01)
*A61L 9/12* (2006.01)

(52) U.S. Cl.
CPC .............. *A61L 9/125* (2013.01); *A61L 9/122* (2013.01); *A61L 2209/11* (2013.01)

(58) Field of Classification Search
USPC .......................................................... 239/34
See application file for complete search history.

(56) References Cited

U.S. PATENT DOCUMENTS

| | | | |
|---|---|---|---|
| 5,023,020 A | 6/1991 | Machida et al. | |
| 5,805,768 A | 9/1998 | Schwartz et al. | |
| D459,950 S | 7/2002 | Bush et al. | |
| 6,581,915 B2 | 6/2003 | Bartsch et al. | |
| 6,834,847 B2 | 12/2004 | Bartsch et al. | |
| D504,171 S | 4/2005 | Ibarra et al. | |
| 7,160,515 B2 | 1/2007 | Murdell et al. | |
| 7,223,361 B2 | 5/2007 | Kvietok et al. | |
| 7,610,118 B2 * | 10/2009 | Schramm et al. | 700/283 |
| 7,691,336 B2 * | 4/2010 | Westring | 422/125 |
| 7,824,627 B2 * | 11/2010 | Michaels et al. | 422/128 |
| 8,296,993 B2 * | 10/2012 | Modlin et al. | 43/132.1 |
| 2002/0066967 A1 * | 6/2002 | Bartsch | A01M 1/2033 261/26 |
| 2007/0199952 A1 * | 8/2007 | Carpenter et al. | 222/52 |
| 2010/0059602 A1 * | 3/2010 | Chiou | A01M 1/2038 239/70 |
| 2011/0027124 A1 * | 2/2011 | Albee et al. | 422/5 |
| 2013/0049236 A1 * | 2/2013 | Garon et al. | 261/26 |

* cited by examiner

*Primary Examiner* — Len Tran
*Assistant Examiner* — Adam J Rogers
(74) *Attorney, Agent, or Firm* — Sterne, Kessler, Goldstein & Fox P.L.L.C.

(57) ABSTRACT

A fragrance dispensing device includes a housing, a fragrance assembly, a cover panel, a fan, and a drive assembly. The housing includes a first portion and a second portion, which moves relative to the first portion. The housing includes an intake opening and an exhaust opening. The fragrance assembly rotates within the housing's interior cavity and defines a plurality of receptacles for receiving fragrance inserts. The cover panel substantially seals one or more receptacles and defines an opening. The fan is coupled to the housing's second portion. The drive assembly rotates the fragrance assembly such that at least a portion of a user-selected fragrance insert is aligned with the cover panel's opening. The fan moves air from the housing's intake opening, across the cover panel's opening, and out the housing's exhaust opening, thereby releasing a fragrance into an environment. The drive assembly may include a shaft with helical threads.

22 Claims, 8 Drawing Sheets

FRAGRANCE DISPENSING DEVICES AND METHODS

BACKGROUND

1. Field

The present invention relates generally to devices that dispense a fragrance into an environment.

2. Background

Home owners and businesses owners sometimes desire that an environment have a certain fragrance. For example, homeowners may want to create a pleasant smelling environment free of odors associated with cooking, pets, cigarette smoke, and other odor sources. Accordingly, devices have been developed that can dispense a certain fragrance into an environment, for example, a room. But after a certain amount of time, people become used to the dispensed fragrance, and the fragrance is not as noticeable as it first was. Other times a person becomes tired or dislikes a certain dispensed fragrance and desires a different fragrance.

Accordingly, there is a need for a device that can selectively dispense two or more fragrances into the environment.

BRIEF SUMMARY

In one embodiment, a fragrance dispensing device includes a housing defining an interior cavity. The housing can include a first portion and a second portion. The second portion can move relative to the first portion between an open position and a closed position. The housing can also define an intake opening and an exhaust opening. The fragrance dispensing device can also include a fragrance assembly rotatably mounted within the interior cavity of the housing. The fragrance assembly defines a plurality of receptacles for receiving fragrance inserts. Further, the fragrance dispensing device includes a cover panel configured to substantially seal one or more receptacles. The cover panel defines an opening. The fragrance dispensing device includes a fan having an intake and an exhaust. The fan is coupled to the second portion of the housing. Additionally, the fragrance dispensing device includes a drive assembly configured to rotate the fragrance assembly such that at least a portion of a user-selected fragrance insert is aligned with the opening of the cover panel. The fan is configured to move air from the intake opening of the housing, across the opening in the cover panel, and out the exhaust opening in the housing, thereby releasing a fragrance into an environment.

In another embodiment, a fragrance dispensing device includes a housing defining at interior cavity, and a fragrance assembly mounted within the interior cavity of the enclosure. The fragrance assembly is configured to rotate about a first axis and has a substantially circular periphery. The periphery of the fragrance assembly has a plurality of teeth. The fragrance assembly defines a plurality of receptacles for receiving fragrance inserts. The fragrance dispensing device also includes a drive assembly comprising a shaft having threads. The drive assembly being configured to selectively rotate the shaft about a second axis that is substantially perpendicular to the first axis. The drive assembly is positioned such that the threads of the shaft mesh with the teeth of the fragrance assembly. The rotation of the shaft about the second axis causes rotation of the fragrance assembly about the first axis.

In one embodiment, a fragrance dispensing device includes a housing having a dimension and defining an interior cavity, and a fragrance assembly rotatably mounted within the interior cavity of the housing. The fragrance dispensing device may also have a drive assembly comprising a motor configured to rotate a drive element. The drive assembly is configured to change a direction of rotation from the drive element to the fragrance assembly by about 90 degrees. The housing has a low profile along the dimension, and the dimension is substantially parallel to an axis of rotation of the fragrance assembly.

In another embodiment, a fragrance insert includes a main body portion having a first side and a second side. The fragrance insert also includes a plurality of spaced apart ribs extending from the first side of the main body portion. The main body portion and the plurality of spaced apart ribs comprise a fragrance infused polymer.

In one embodiment, a fragrance dispensing device may include a housing defining an interior cavity. The housing may include a first portion and a second portion that is movable relative to the first portion between an open position and a closed position. The housing may include an intake opening and an exhaust opening. The fragrance dispensing device may also include a fragrance assembly rotatably mounted within the interior cavity of the housing. The fragrance assembly defines a plurality of receptacles for receiving one or more fragrance inserts. The fragrance dispensing device also includes a cover panel configured to substantially seal one or more receptacles of the plurality of receptacles. The cover panel defines an opening. The fragrance dispensing device includes a fan having an intake and an exhaust, the fan being coupled to the first portion of the housing. The fan is configured to move air from the intake opening of the housing, across the opening in the cover panel, and out the exhaust opening in the housing, thereby releasing a fragrance into an environment. The housing defines an opening, and the fragrance assembly is positioned such that a portion of the fragrance assembly extends through the opening to an exterior of the housing. A user can selectively rotate the fragrance assembly by contacting the exposed portion of the fragrance assembly.

In another embodiment, a fragrance dispensing device includes a housing defining an interior cavity, a fragrance assembly, a cover panel, and a fan. The housing includes a first portion and a second portion. The second portion moves relative to the first portion between an open position and a closed position. The housing has an intake opening and an exhaust opening. The fragrance assembly is mounted within the interior cavity of the housing and defines a plurality of receptacles for receiving one or more fragrance inserts. The cover panel is configured to substantially seal one or more receptacles of the plurality of receptacles. The cover panel also defines an opening and is rotatably mounted within the interior cavity of the housing. The fan has an intake and an exhaust. The fan is coupled to the first portion of the housing. And the fan is configured to move air from the intake opening of the housing, across the opening in the cover panel, and out the exhaust opening in the housing, thereby releasing a fragrance into an environment.

Further embodiments, features, and advantages of the present invention, as well as the structure and operation of the various embodiments of the present invention, are described in detail below with reference to the accompanying drawings.

BRIEF DESCRIPTION OF THE DRAWINGS

The accompanying drawings, which are incorporated herein and form a part of the specification, illustrate embodiments of the present invention and, together with the description, further serve to explain the principles of the invention and to enable a person skilled in the pertinent art to make and use the invention.

The embodiments of present invention will be described with reference to the accompanying drawings. The drawing in which an element first appears is typically indicated by the leftmost digit(s) in the corresponding reference number. In the drawings, like reference numbers generally indicate identical, functionally similar, and/or structurally similar elements.

DETAILED DESCRIPTION OF THE INVENTION

While specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

The embodiments described, and references in the specification to "one embodiment," "an embodiment," "an example embodiment," etc., indicate that the embodiments described may include a particular feature, structure, or characteristic, but every embodiment may not necessarily include the particular feature, structure, or characteristic. Moreover, such phrases are not necessarily referring to the same embodiment. Further, when a particular feauture, structure, or characteristic is described in connection with an embodiment, it is understood that it is within the knowledge of one skilled in the art to effect such feature, structure, or characteristic in connection with other embodiments whether or not explicitly described.

Figure 1:
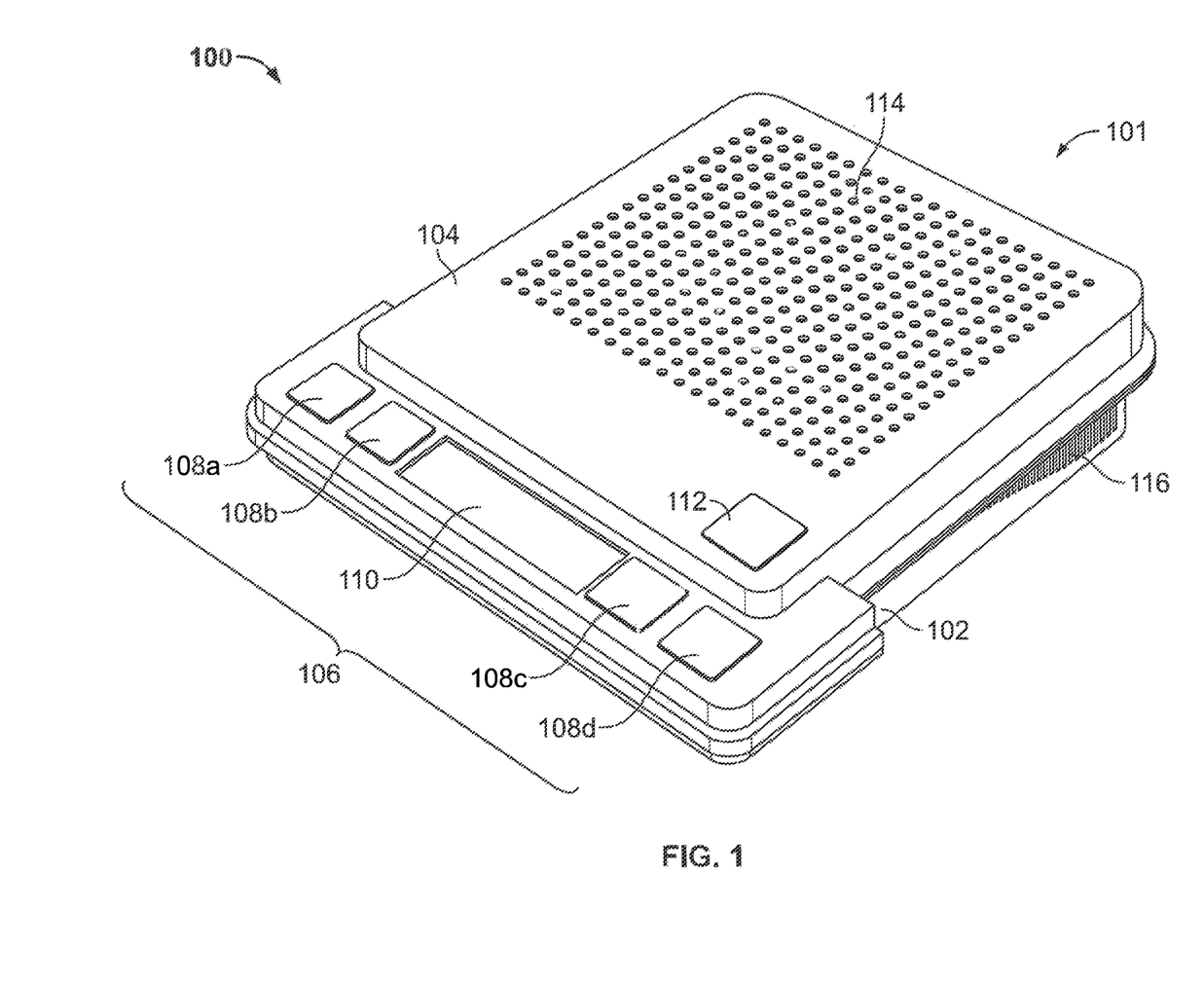
FIG. 1 is perspective view of a fragrance dispensing device in a closed position according to an embodiment of the present invention.

In some embodiments, a fragrance dispensing device is configured to allow a user to select a fragrance to release into an environment, for example, a room, from a plurality of available fragrances. In some embodiments, a fragrance dispensing device may include a housing, a fragrance assembly for receiving a plurality of fragrance inserts that is rotatably mounted within the housing, a drive assembly for selectively rotating the fragrance assembly, and a fan for creating an air flow. FIG. 1 is perspective view of a fragrance dispensing device 100 according to one embodiment.

Fragrance dispensing device 100 may include a housing 101 defining an interior cavity. Housing 101 is configured to enclose, or at least partially enclose, the internal components of fragrance dispensing device 100 that are contained within the interior cavity of housing 101. Housing 101 can be any suitable shape. For example, housing 101 can have a substantially rectangular prism shape, pyramid shape, semi-hemisphere shape, or any other suitable three dimensional polygonal or curvi-linear shape.

In one embodiment, housing 101 may include a first portion 102 and a second portion 104. In some embodiments, first portion 102 and second portion 104 can generally form halves of housing 101 as shown in FIG. 1. Housing 101 can have any suitable shape. In some embodiments, housing 101 may be configured such that fragrance dispensing device 100 can be easily placed on a horizontal surface, for example, a table top. In some embodiments, housing 101 can be configured such that that fragrance dispensing device 100 can be mounted to a vertical surface, for example, a wall. In some embodiments, first portion 102 may be a base, and second portion 104 may be a lid that closes an opening of a cavity defined by first portion 102.

In some embodiments, fragrance dispensing device 100 may also include a user interface 106 on housing 101. User interface 106 may be configured to allow a user to indicate a desired fragrance to be released into the environment. In some embodiments, user interface 106 includes one or more fragrance selection buttons, for example, two, three, four, five, or more than five fragrance selection buttons. For example, user interface 106 may include four fragrance selection buttons 108a, 108b, 108c, and 108d as shown in FIG. 1. Each fragrance selection buttons 108a, 108b, 108c, and 108d is associated with a certain fragrance. Fragrance dispensing device 100 is configured to dispense the fragrance associated with the fragrance selected by the user, for example, by pressing selection buttons 108a, 108b, 108c, or 108d.

User interface 106 may also include a display 110 configured to display information in some embodiments. For example, display 110 can be a LED device, LCD device, electronic paper device, OLED device, or any other suitable display technology configured to display symbols or alphanumeric characters. In some examples, display 110 can be different color LEDs. In some embodiments, display 110 indicates the fragrances available to be dispensed, the fragrance currently being dispensed, duration since the last fragrance dispensing, duration of current fragrance dispensing, or any other suitable information.

In some embodiments, user interface 106 can include a touch screen device. In such embodiments, the fragrance selection buttons can be implemented as soft keys on the touch screen sensitive screen. In some embodiments, the user interface 106 may include a touch sensitive surface for sensing hand gestures and display 110. In such embodiments, a user can select a desired fragrance by making certain hand gestures, and display 110 can indicate the selected fragrance.

Fragrance dispensing device 100 may also include a power button 112. Power button 112 can be located on an exterior surface of housing 101. Power button 112 can activate the fan (described below) to dispense a desired fragrance or to activate the user interface 106 to allow a user to enter a desired input.

Figure 2:
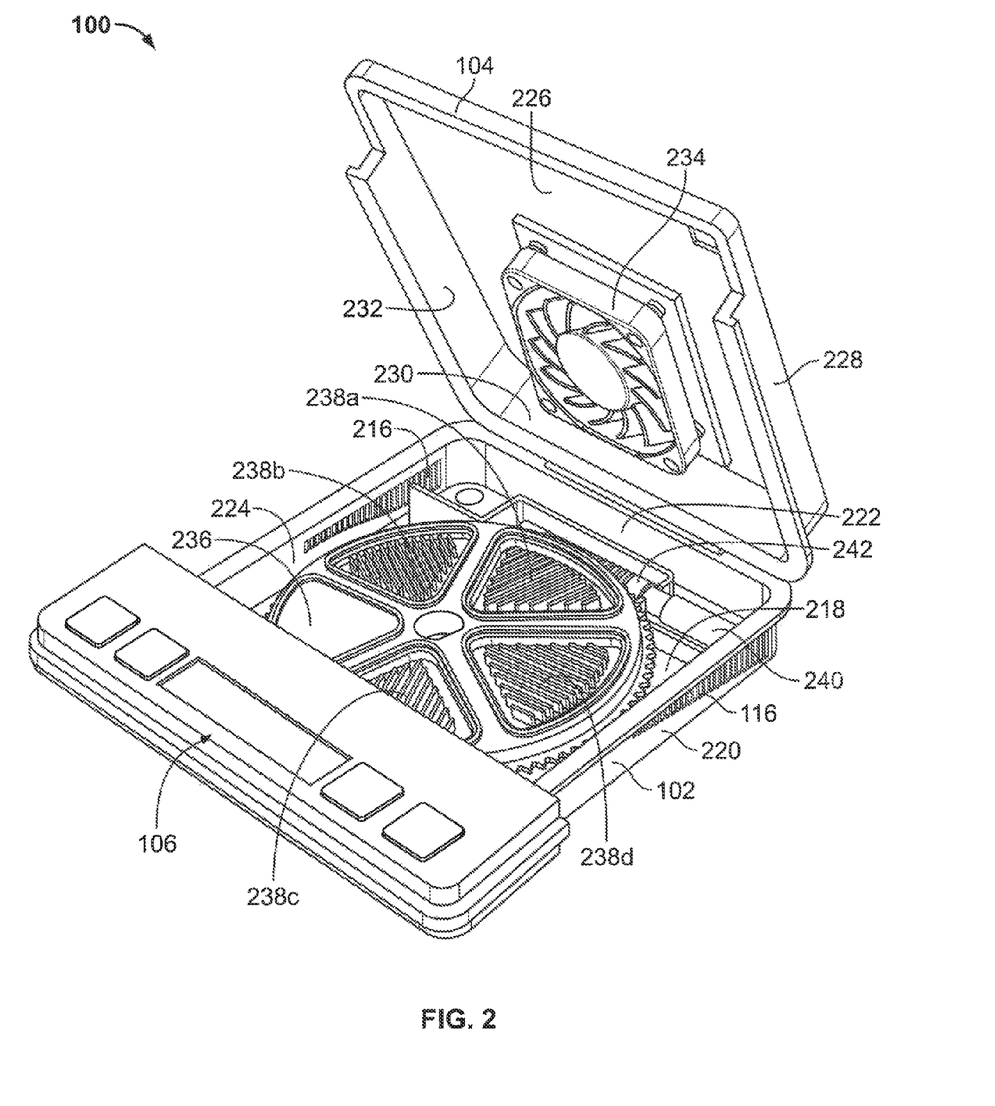
FIG. 2 is a perspective view of the fragrance dispensing device of FIG. 1 in an open position according to an embodiment of the present invention.

Housing 101 may also define one or more exhaust openings 114 and one or more intake openings 116 (and 216 as shown in FIG. 2). As further described below, fragrance dispensing device 100 may be configured to draw air within housing 101 through intake openings 116 and 216 and discharge air from housing 101 through exhaust openings 114. In some embodiments, first portion 102 of housing 101 may define the intake openings 116, and second portion 104 of housing 101 may define the exhaust openings 114. Exhaust openings 114 and intake openings 116 may have any suitable shape, for example, a circular (like exhaust openings 114 shown in FIG. 1), rectangular (like intake openings 116 and 216 shown in FIGS. 1 and 2), triangular, or any other suitable polygonal or curvi-linear shape.

In some embodiments, first portion 102 and second portion 104 may be configured to be movable relative to each other between an open position (for example, as shown in FIG. 2) providing a user access to the interior cavity defined by housing 101 and a closed position (for example, as shown in FIG. 1) substantially preventing access to the interior cavity. In some embodiments, the interface between first portion 102 and second portion 104 in the closed position substantially creates an environmental seal. In some embodiments, second portion 104 can be pivotally coupled to first portion 102 using a hinge or similar device. In some embodiments, second portion 104 is slidably coupled to first portion 102. In some embodiments, second portion 104 can be completely and selectively detached from first portion 102.

Housing 101 can be made of any suitable material. For example, housing 101 can be made from metal, plastic, a combination of metal and plastic, or any other suitable material. In some embodiments, all or a portion of housing 101 may comprise a non gas permeable material.

FIG. 2 is a perspective view of fragrance dispensing device 100 in the open position according to one embodiment. In FIG. 2, the cover panel is removed to better illustrate the fragrance assembly. As shown in FIG. 2, first portion 102 is angled relative to second portion 104, which provides access to the interior cavity defined by housing 101. In some embodiments, first portion 102 of housing 101 may include a first panel 218 and one or more side panels extending away from first panel 218 to define at least a portion of the interior cavity. In some embodiments, first portion 102 includes a first side panel 220 extending from one edge of first panel 218, a second side panel 222 extending from another edge of first panel 218, and a third side panel 224 extending from yet another edge of first panel 218. In some embodiments, first panel 218 is a rectangle, circle, triangle, or any other suitable polygonal or curvi-linear shape. First panel 218 may be planar or non-planar.

In some embodiments, first side panel 220 may define the intake openings 116. As shown in FIG. 2, housing 110 may also include one or more second intake openings 216 in some embodiments. Third side panel 224 may define intake openings 216 in some embodiments.

As shown in FIG. 2, second portion 104 of housing 101 may include a first panel 226 and one or more side panels extending away from first panel 226 to define at least a portion of the interior cavity of the housing 101. In some embodiments, second portion 104 includes a first side panel 228 extending from one edge of first panel 226, a second side panel 230 extending from another edge of first panel 226, and a third side panel 232 extending from yet another edge of first panel 226. In some embodiments, first panel 218 is rectangular, circular, triangular, or any other suitable polygonal or curvilinear shape. As best seen in FIG. 1, first panel 226 may define the plurality of exhaust openings 114 in some embodiments. In some embodiments, side panel 222 of first portion 102 is pivotally coupled to side panel 230 of second portion 104. Accordingly, second portion 104 can rotate between the closed position (FIG. 1) and the open position (FIG. 2).

In some embodiments, fragrance dispensing device 100 may also include a fan 234 or any other suitable device for creating fluid flow. Fan 234 can be positioned and arranged to create an air flow such that air enters the interior cavity of housing 101 through intake openings 116 and 216 and exits through exhaust openings 114. Fan 234 may have an intake and an exhaust. The exhaust of fan 234 may be in fluid communication with exhaust openings 114 defined by second portion 104. In some embodiments, the exhaust of fan 234 is adjacent openings 114. In some embodiments, the exhaust fan 234 is spaced away from exhaust openings 114 of second portion 104, and is in fluid communication with exhaust openings 114 via one or more ducts. In some embodiments, fan 234 can be an axial-flow fan (as shown in FIG. 2), a centrifugal fan, a cross flow fan, or any other suitable fan device. In some embodiments, fan 234 may be coupled to second portion 104 of housing 101. For example, fan 234 can be coupled to an inner surface of first panel 226 of second portion 104. In such embodiments in which second portion 104 is connected to first portion 102 using a hinge, fan 234 rotates along with second portion 104 about the axis of the hinge.

Fragrance dispensing device 100 includes a fragrance assembly 236. Fragrance assembly 236 may be rotatably mounted within the interior cavity of housing 101. Fragrance assembly 236 may be configured to securely receive one or more fragrance inserts. For example, fragrance assembly 236 may hold four fragrance inserts 238a, 238b, 238c, and 238d in some embodiments as shown in FIG. 2. In some embodiments, each fragrance insert 238a, 238b, 238c, or 238d has a unique fragrance. In some embodiments, fragrance assembly 236 is removably mounted within housing 101. In such embodiments, fragrance assembly 236 and fragrance inserts 238a, 238b, 238c, or 238d can be easily replaced. In some embodiments, as shown FIGS. 2-4, fragrance assembly 236 is a substantially circularly disc that rotates about an axis.

In some embodiments, fragrance assembly 236 is configured to rotate about an axis substantially perpendicular to first panel 218 of first portion 102. In some embodiments, the axis about which the fragrance assembly rotates is aligned with the axis of fan 234.

Fragrance dispending device 100 may also include a drive assembly configured to selectively rotate fragrance assembly 236. The drive assembly may be securely coupled within the interior cavity of housing 101. In some embodiments, the drive assembly may include a controller (not shown), a motor 240, and a shaft 242. The controller controls the actuation of motor 240. The controller can be a microprocessor, discrete circuits on motor 240, analog circuits, or any other suitable controlling device. In some embodiments, the controller can be the same microprocessor used with user interface 106.

Motor 240 is configured to rotate one or more drive element(s) operatively coupled with fragrance assembly 236. In some embodiments, motor 240 can be an electrical motor. For example, motor 240 can be a DC motor, an AC motor, or any other suitable motor (e.g., a stepper motor) that can be configured to rotate the drive element(s).

In some embodiments, the drive element may be an elongated shaft 242 having helical threads, for example, a worm shaft, that rotates about an axis. Threaded shaft 242 may be configured to mesh with teeth on fragrance assembly 236 (further described below). In some embodiments, motor 240 is coupled to first portion 102 of housing 101 by any suitable means, for example, by using fasteners, adhesives, a snap fit, etc. In some embodiments, a distal end of shaft 242 is rotatably coupled to a bearing mount, which may be fixed to first panel 218 of first portion 102. In some embodiments, the drive assembly can be configured to minimize a dimension, for example, the height, of housing 101. For example, in some embodiments, the axis about which shaft 242 rotates is perpendicular to the axis about which fragrance assembly 236 rotates. In this manner, the axis about which shaft 242 rotates is parallel to a surface of panel 218 of first portion 102 to which fragrance assembly 236 is mounted. In such an example, housing 101 has a low-dimension profile, for example, a low height-profile as shown in FIGS. 1 and 2. As shown in FIGS. 1-2, the height dimension of housing 101 is substantially parallel to the axis of rotation of fragrance assembly 236.

In some embodiments, the drive element may be a helical gear. In some embodiments, the drive assembly is configured to change the direction of rotation from the drive element to the fragrance assembly 236 by about 90 degrees. In some embodiments, such 90 degree configurations allow for a low profile of housing 101 along a dimension that is substantially parallel to the axis of rotation of fragrance assembly 236.

The controller is configured to receive the user input from user interface 106 and accordingly control the actuation of motor 240 and rotation of the drive element(s), for example, shaft 242. Thus, the controller can ultimately control rotation of fragrance assembly 236 that is operatively coupled to the drive element(s).

In some embodiments, instead of shaft 242, the drive assembly includes one or more gears operatively coupled to a shaft of motor 240 and the teeth of fragrance assembly 236.

Figure 11:
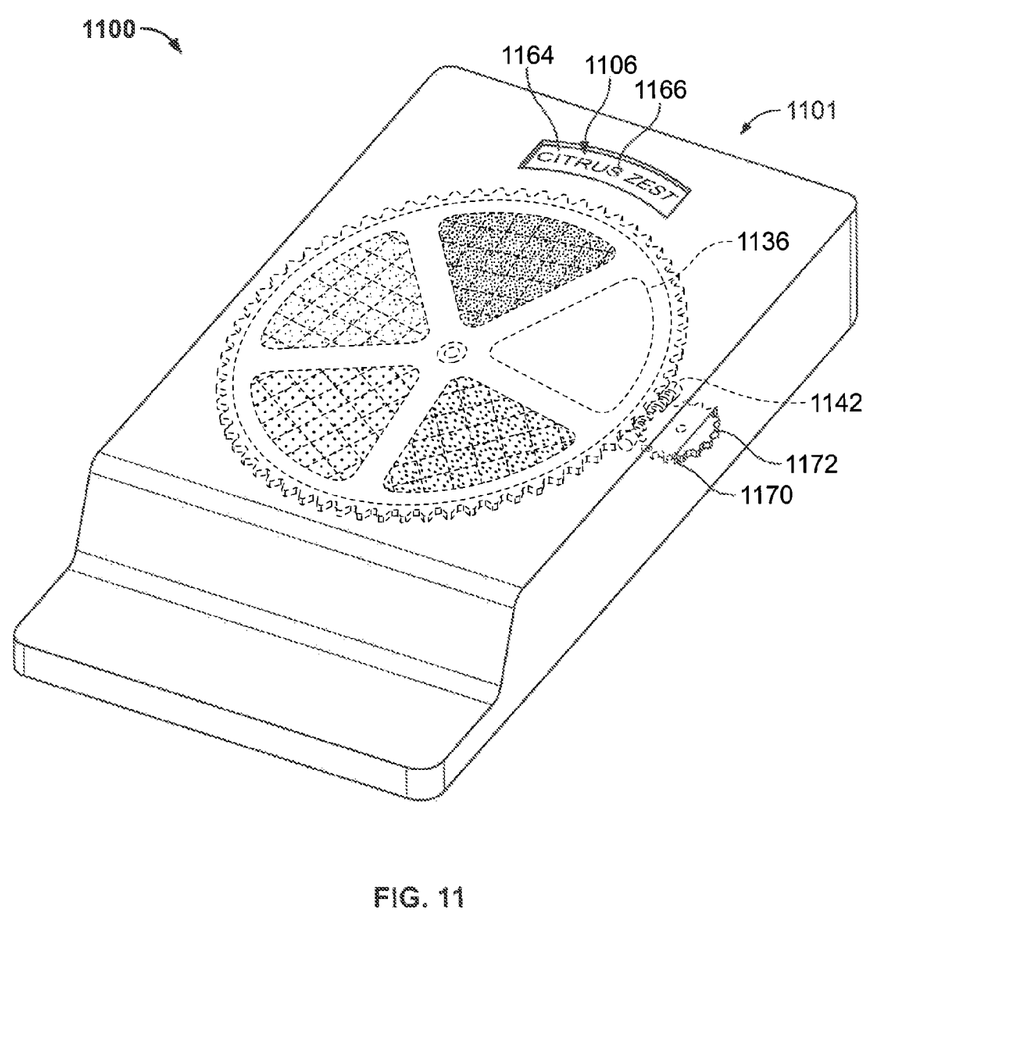
FIG. 11 is a schematic perspective view of a fragrance dispensing device with the fan removed for illustrative purposes according to yet another embodiment of the present invention.

In some embodiments, the drive assembly may be configured to manually rotate fragrance assembly 236. For example, in some embodiments, instead of motor 240, a thumb gear may be coupled to shaft 242 that is operatively coupled to fragrance assembly 236. For example, as shown in FIG. 11, a fragrance dispensing device 1100 may include a housing 1101 that defines an opening 1170. Opening 1170 may be defined in a side panel of housing 1101, for example. The drive assembly may include a thumb gear 1172 and a threaded shaft 1142. Thumb gear 1172 may be rotatably mounted within the cavity defined by housing 1101 and positioned such that at least a portion of thumb gear 1172 extends through opening 1170 to an exterior of housing 1101. The teeth of thumb gear 1172 are operatively coupled with the threads of shaft 1142, and the threads of shaft 1142 are also operatively coupled with the teeth of a fragrance assembly 1136, which is rotatably mounted within housing 1101. A user can selectively rotate the exposed portion of thumb gear 1172, which rotates shaft 1142 which in turn rotates fragrance assembly 1136. In some embodiments, the manual drive assembly may include a gear or wheel assembly that does not include shaft 1142. For example, thumb gear 1172 may be operatively coupled directly to fragrance assembly 1136.

Figure 3:
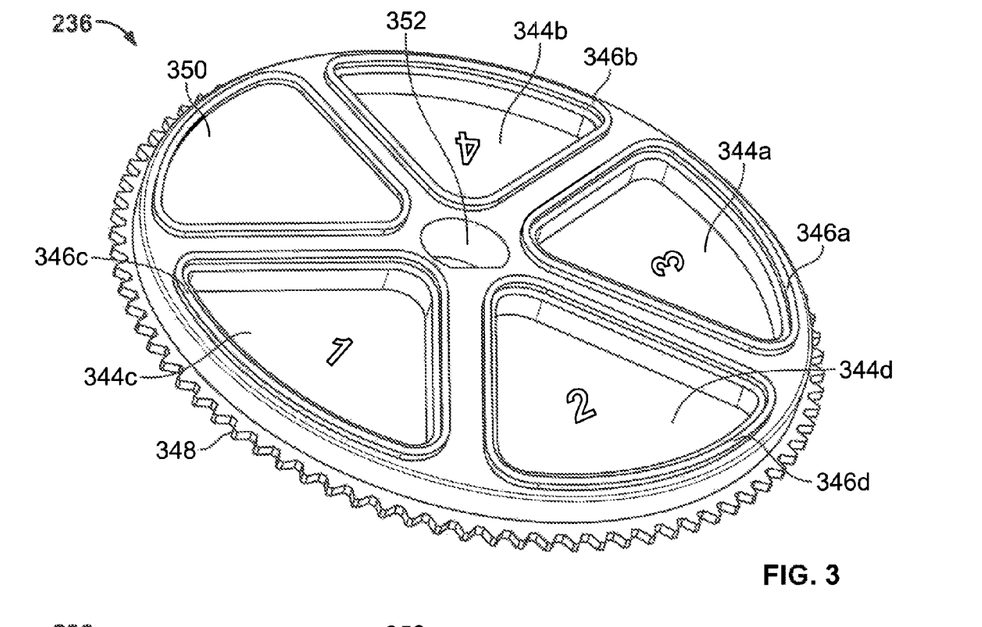
FIG. 3 is a perspective view of a fragrance assembly for receiving fragrance inserts according to an embodiment of the present invention.
Figure 4:
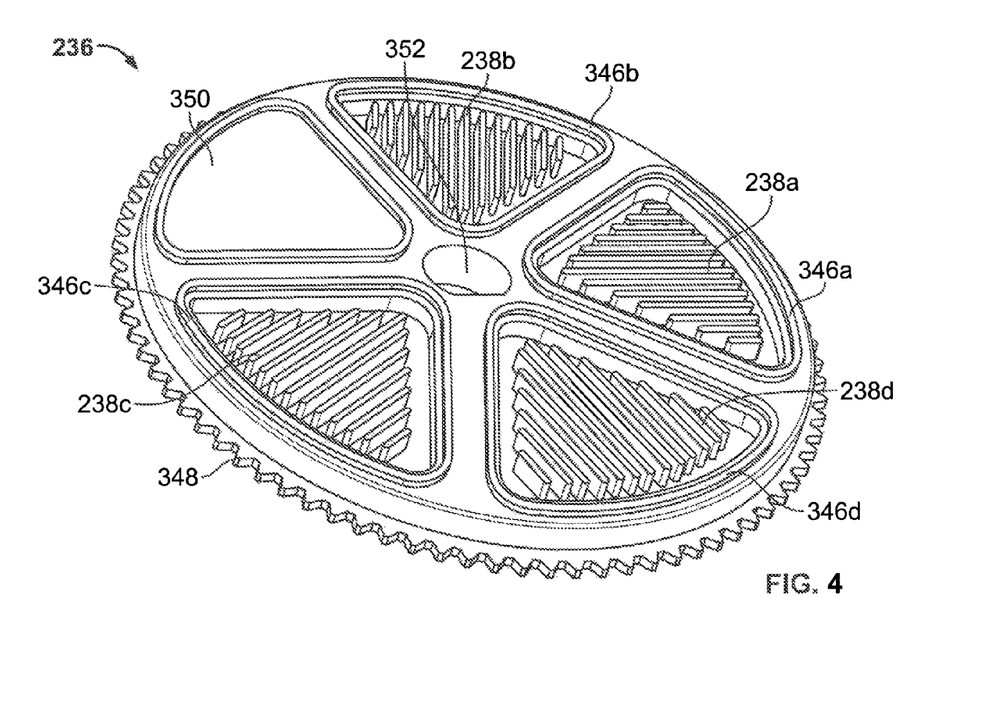
FIG. 4 is a perspective view of the fragrance assembly of FIG. 3 with fragrance inserts according to an embodiment of the present invention.

FIG. 3 is a perspective view of fragrance assembly 236 without fragrance inserts according to an embodiment. In some embodiments, fragrance assembly 236 defines a plurality of recessed receptacles for receiving fragrance inserts. As shown in FIG. 3, fragrance assembly 236 may define four receptacles 344a, 344b, 344c, and 344d. Receptacles 344a, 344b, 344c, and 344d may have a shape that substantially corresponds to the shape of fragrance inserts 238a, 238b, 238c, and 238d. In some embodiments, receptacles 344a, 344b, 344c, and 344d are sized to create a snap-fit or a friction fit with fragrance inserts 238a, 238b, 238c, and 238d. Fragrance assembly 236 may also include a portion that is not configured to receive a fragrance insert, for example, a flat panel 350 as shown in FIG. 3. In some embodiments, receptacles 344a, 344b, 344c, and 344d and flat panel 350 are equally spaced about the axis of rotation of the fragrance assembly 236. In some embodiments, receptacles 344a, 344b, 344c, and 344d are the same size and shape.

In some embodiments, fragrance assembly 236 can be rotatably mounted within the interior cavity of housing 101 via a post and opening interface. For example, fragrance assembly 236 may define a central aperture 352 as shown FIG. 3. Aperture 352 can be sized to closely receive a post (not shown) extending from a surface of first portion 102, for example, a post extending from first panel 218.

In some embodiments, fragrance assembly 236 may include a gasket that surrounds one or more receptacles of fragrance assembly 236. For example, fragrance assembly 236 may include four gaskets 346a, 346b, 346c, and 346d that surround receptacles 344a, 344b, 344c, and 344d, respectively. Gaskets 346a, 346b, 346c, and 346d are configured to substantially create a sealed environment around fragrance inserts 238a, 238b, 238c, and 238d as further discussed below. In some embodiments, each gasket 346a, 346b, 346c, and 346d is formed from rubber, silicone, neoprene, a plastic polymer, or any other suitable material.

In some embodiments, fragrance assembly 236 is a substantially circular tray or disc that has teeth 348 surrounding the circular periphery of fragrance assembly 236. Teeth 348 are configured to mesh with the drive element of the drive assembly, for example, threaded shaft 242 as shown in FIG. 2, such that rotation of the drive element rotates fragrance assembly 236. For example, in some embodiments, if threaded shaft 242 is a worm shaft, fragrance assembly 236 forms a worm wheel.

Figure 5:
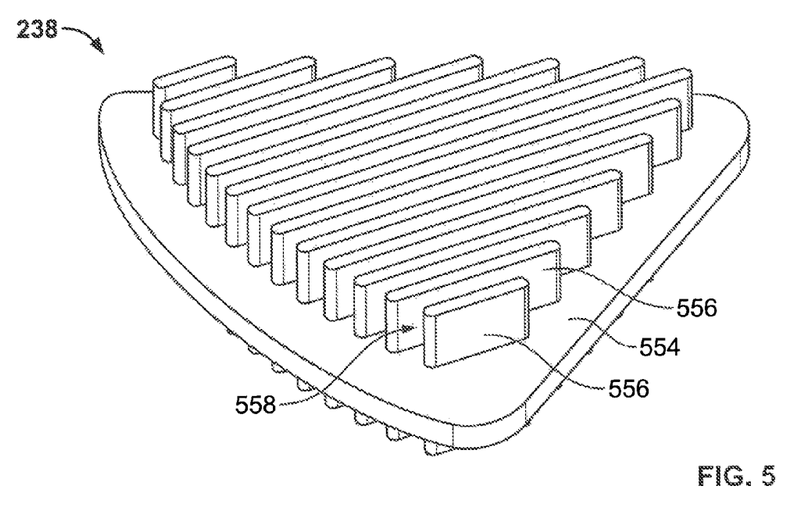
FIG. 5 is a perspective view of a fragrance insert according to an embodiment.

FIG. 5 is a perspective view of a fragrance insert 238 according to an embodiment. As shown in FIG. 5, fragrance insert 238 can have a substantially circular sector shape. In other embodiments, fragrance insert 238 can have other suitable shapes, for example, a circle, rectangle, a triangle, or any other suitable polygonal or curvi-linear shape.

In some embodiments, fragrance insert 238 may be a fragrance infused polymer insert. In some embodiments, fragrance insert 238 may include a main body portion 554 that has a first side and a second side. Fragrance insert 238 may also include one or more ribs 556 extending from the first side of main body portion 554. Ribs 556 define a plurality of channels 558 between each pair of ribs 556. Ribs 556 increase the surface area of fragrance insert 238 exposed to the air flow, which increases the strength of the fragrance discharged from fragrance dispensing device 100. In some embodiments, fragrance insert 238 may also include one or more ribs 556 extending from the other side of main body portion 554.

Figure 9:
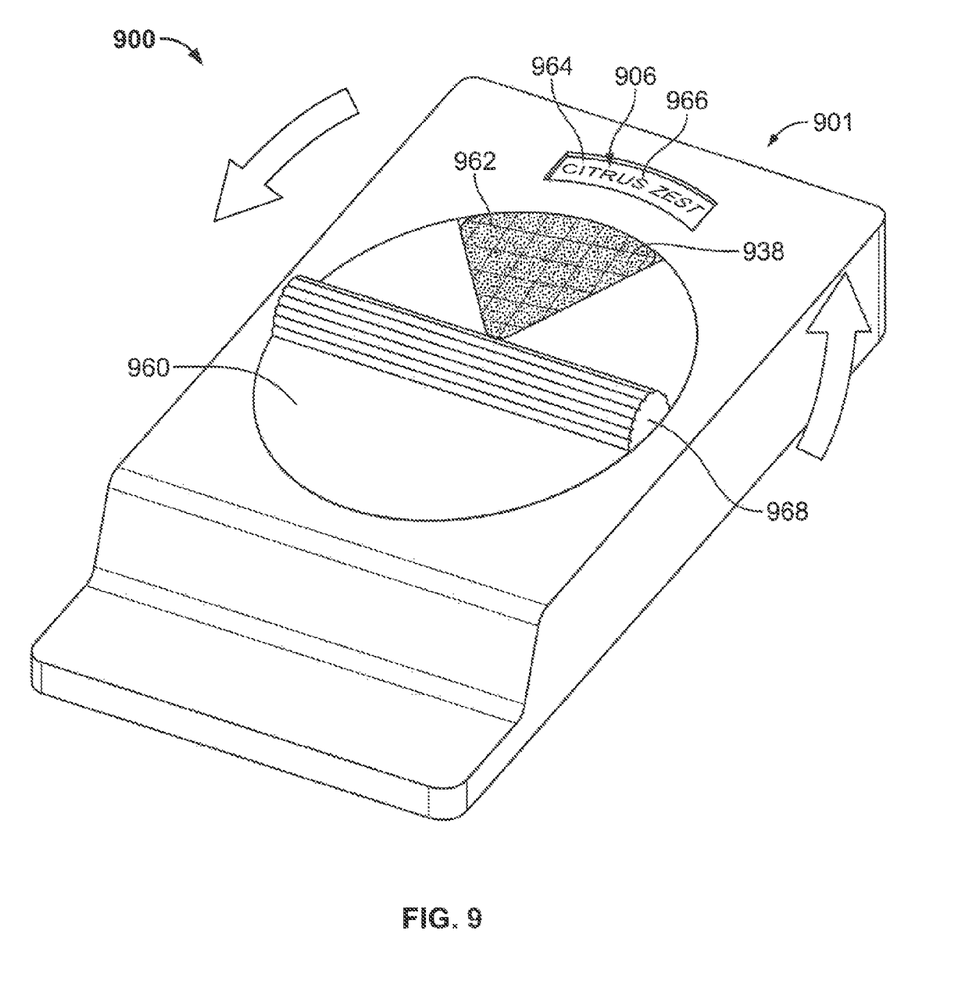
FIG. 9 is a schematic perspective view of a fragrance dispensing device with a portion of the housing cut away and with the fan removed for illustrative purposes according to another embodiment of the present invention.
Figure 10:
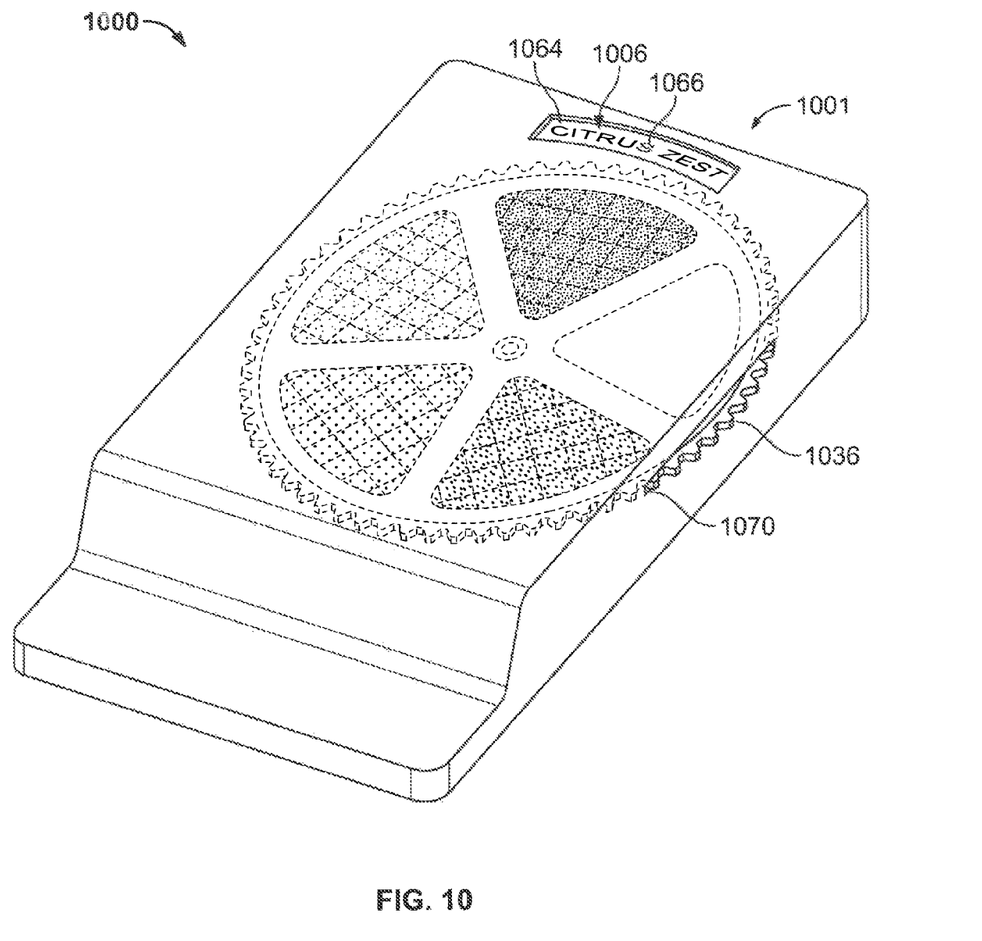
FIG. 10 is a schematic perspective view of a fragrance dispensing device with the fan removed for illustrative purposes according to another embodiment of the present invention.

In some embodiments (see FIGS. 9-11), the fragrance insert may include a plurality of fragrance pellets, for example, fragrance infused polymer pellets, contained within a casing (see FIGS. 9-11). The casing may include at least one surface configured to allow air that is drawn into the interior cavity of housing by the fan to interface with the fragrance pellets. For example, the surface may comprise a solid surface defining a plurality of through holes, a mesh-type or cage-like surface, or any other suitable surface that allows air to pass.

In some embodiments, fragrance insert 238 may include a volatile gel or any other suitable fragrance eluting material.

Fragrance inserts 238a, 238b, 238c, and 238d can have a variety of fragrances. In some embodiments, fragrance inserts 238a, 238b, 238c, and 238d can have a fragrance associated with holiday seasons (for example, Thanksgiving, Christmas, or other holidays), physiological states (for example, relaxation, concentration, or other physiological states), themes (for example, floral, forest, mountains, flowers, or other themes), a room location (for example, a kitchen, bathroom, dining room, or another room), or any other desired fragrance category. In some embodiments, the fragrances of each fragrance insert 238a, 238b, 238c, and 238d are all within a similar category of fragrances. For example, fragrance assembly 236 can include fragrance insert 238a, 238b, 238c, and 238d that each has different floral fragrances. In other embodiments, the fragrances of each fragrance insert 238a, 238b, 238c, and 238d are not all within a similar category of fragrances.

Figure 6:
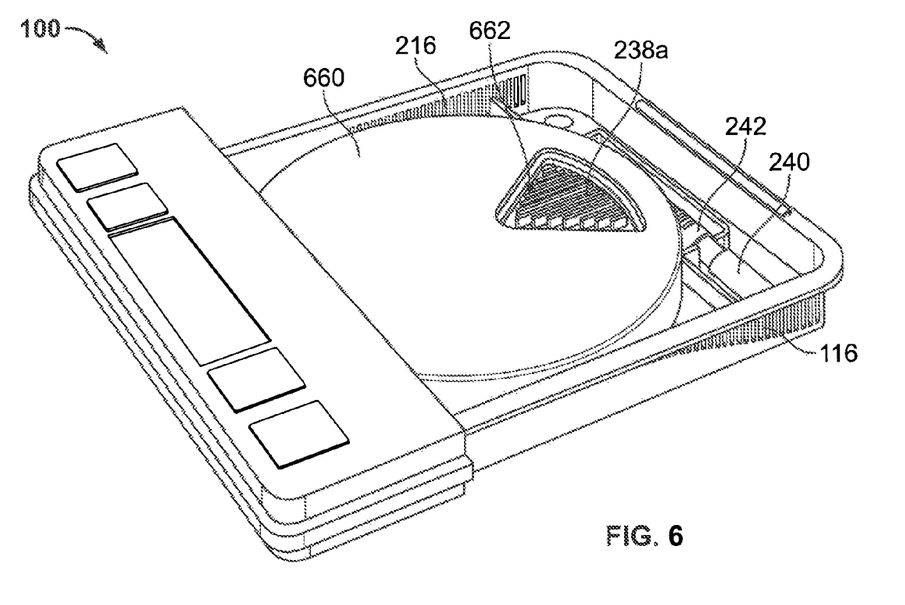
FIG. 6 is a perspective view of the fragrance dispensing device of FIGS. 1 and 2 with a portion of the housing removed according to an embodiment of the present invention.

FIG. 6 illustrates a perspective view of fragrance dispensing device 100 with second portion 104 removed to better illustrate the internal components. As shown in FIG. 6, fragrance dispensing device 100 may also include a cover panel 660. Cover panel 660 defines an opening 662. In some embodiments, the shape opening 662 substantially corresponds to the shape of fragrance inserts 238a, 238b, 238c, and 238d. For example, opening 662 can have a circular sector shape. Fragrance dispensing device 100 is configured such that fragrance assembly 236 rotates relative to cover panel 660. For example, in some embodiments, cover panel 660 remains stationary while fragrance assembly 236 rotates. In some embodiments, cover panel 660 is positioned and arranged not to interfere with the engagement of the driving element, for example, shaft 242, of the drive assembly and teeth 348 of fragrance assembly 236. In some embodiments, cover panel 660 is positioned such that a seal is substantially created between a surface facing fragrance assembly 236 and gaskets 346a, 346b, 346c, and 346d. Opening 662 allows the air flowing from intake openings 116 and 216 to interface with the fragrance insert, for example, fragrance insert 238a as shown in FIG. 6, aligned with opening 662. The fragrance of the aligned fragrance insert is, thus, discharged to the environment. The seal between cover panel 660 and gaskets 346a, 346b, 346c, and 346d prevents the air flow from interfacing with the fragrance inserts not aligned with opening 662, for example, fragrance inserts 238b, 238c, and 238d.

Figure 7:
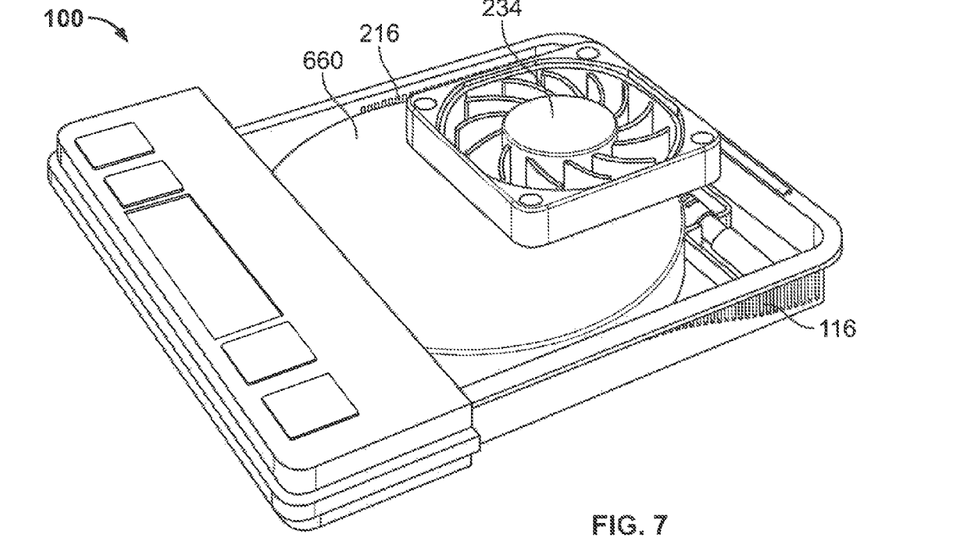
FIG. 7 is a perspective view of the fragrance dispensing device of FIGS. 1, 2, and 6 with the housing portion removed and illustrating a fan according to an embodiment of the present invention.
Figure 8:
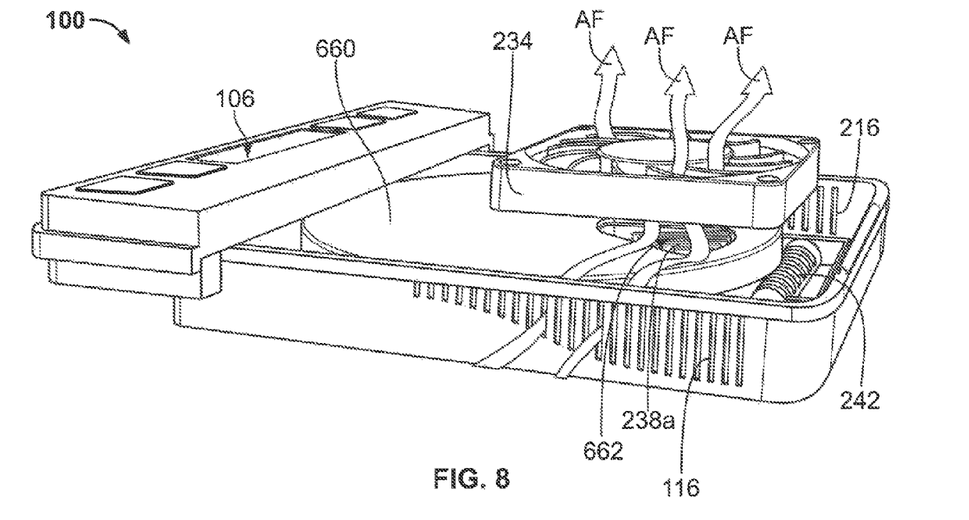
FIG. 8 is a side perspective view of the fragrance dispensing device of FIGS. 1, 2, 6, and 7 with the housing portion removed and illustrating a fan according to an embodiment of the present invention.

FIGS. 7 and 8 illustrate a perspective view and a side perspective view, respectively, of fragrance dispensing device 100. Although second portion 104 is omitted for illustrative purposes, these views show the position fan 234 when second portion 104 is in the closed position. As shown in FIG. 7, the intake of fan 234 is substantially aligned with opening 662 of cover panel 660 when second portion 104 is in the closed position. Accordingly, when fan 234 is activated, fan 234 air flows (illustrated as arrows AF in FIG. 8) into the interior cavity of housing 101 through intake openings 116 and 216 of housing 101 and across opening 662 of cover panel 660 allowing the air to interface with the fragrance insert aligned with opening 662. The air then flows through the intake of fan 234 and out the exhaust of fan 234, exiting housing 101 through exhaust openings 114. The discharged air that exits exhaust openings 114 delivers the fragrance of the fragrance insert aligned with opening 662 into the environment. The seals created between cover panel 660 and gaskets 346a, 346b, 346c, and 346d substantially prevent the air flow from interfacing with the fragrance insert not aligned with opening 662. Accordingly, the fragrance associated with the fragrance insert aligned with opening 662 is delivered to the environment.

In operation, a user can select a desired fragrance by using user interface 106. In some embodiments, display 110 indicates the available fragrances associated with fragrance inserts 238a, 238b, 238c, and 238d. In some embodiments, fragrance assembly 236 may include a transmitter configured to transmit a signal containing information regarding the fragrance inserts 238a, 238b, 238c, and 238d contained on fragrance assembly 236, for example, the specific fragrance associated with each insert, the category of fragrances, or any other desired information about fragrance assembly 236 or fragrance inserts 238a, 238b, 238c, and 238d. For example, the transmitter can be an RFID tag or any other suitable transmitter. In such embodiments, fragrance dispensing device 100 may also include a receiver configured to receive the signal transmitted from the transmitter of fragrance assembly 236. For example, the receiver can be an RFID reader or any other suitable signal receiver. Fragrance dispensing device 100 can be configured to use the information received from the transmitter of fragrance assembly 236 and indicate that information on display 110.

If the fragrance selected by the user is not the fragrance of the fragrance insert aligned with opening 662 of cover panel 660, the drive assembly controller actuates motor 240, causing the drive element, for example, shaft 242, to rotate. Rotation of the drive element, for example, shaft 242, causes fragrance assembly 236 to rotate. Motor 240 is actuated until the fragrance insert that is associated with the user's selection is aligned with opening 662 of cover panel 660.

In some embodiments, the drive assembly controller actuates motor 240 after predetermined time periods, for example, every hour, to align the next fragrance insert with opening 662 of cover panel 660.

In some embodiments, fan 234 can be powered on and off manually using power button 112. In other embodiments, fragrance dispensing device 100 automatically controls the operation of fan 234 according to predefined operation conditions when a fragrance is selected.

In some embodiments, the fragrance inserts 238a, 238b, 238c, and 238d can be replaced after their useful life. In some embodiments, replacement can be achieved by moving second portion 104 of housing 101 to the open position as shown in FIG. 2. The old fragrance assembly 236 can be removed from housing 101 and replaced with a new fragrance assembly 236 with fresh fragrance inserts. In some embodiments, instead of replace the older fragrance assembly 236 with an entirely new fragrance assembly 236, just the fragrance inserts 238a, 238b, 238c, and 238d can be replaced.

In some embodiments, fragrance dispensing device 100 is connected to an external power source, for example, an AC or DC power source, using a power cord. In some embodiments, fragrance dispensing device 100 also includes an internal power source, for example, a disposable or replaceable battery.

In some embodiments, a fragrance dispensing device may not include a drive assembly. For example, as shown in FIG. 10, a fragrance dispensing device 1000 may include an enclosure 1001 defining an opening 1070. Opening 1070 may be defined in a side panel of housing 1001. A fragrance assembly 1036 may be rotatably mounted in the interior cavity defined by housing 1001. Fragrance assembly 1036 may be positioned such that at least a portion of fragrance assembly 1036 extends through opening 1070 of housing 1001. A user can selectively and manually rotate the exposed portion of fragrance assembly 1036 to choose the desired fragrance insert.

In some embodiments, with reference to fragrance dispensing device 100, for example, fragrance assembly 236 remains stationary while cover panel 660 rotates. In such embodiments, the drive assembly is modified to rotate cover panel 660 instead of fragrance assembly 236. For example, threaded shaft 242 may be configured to mesh with the teeth on cover panel 660, which is rotatably mounted within housing 101. Accordingly, if the fragrance selected by the user is not the fragrance associated with the fragrance insert aligned with opening 662 of cover panel 660, the drive assembly may be actuated to rotate cover panel 660. The drive assembly is actuated until the fragrance insert that is associated with the user's selection is aligned with opening 662 of cover panel 660.

FIG. 9 illustrates another embodiment of a fragrance dispensing device 900 in which a cover panel 660 rotates. Fragrance dispensing device 900 includes cover panel 960. Cover panel 960 is rotatably mounted to rotate relative to a stationary fragrance assembly that houses fragrance inserts 938. Cover panel 960 may include one or more tabs 968 that extend from a surface of cover panel 960. Tabs 968 are configured and arranged to extend through one or more slots or holes defined in a housing 901. Accordingly, a user may manually apply a force to tabs 968 to rotate cover panel 966 so that an opening defined by cover panel 966 is aligned with a desired fragrance insert 938.

In some embodiments, the user interface may include a manual display, for example, a window defined by a panel of the housing. For example, user interfaces 906, 1006, and 1106 of fragrance dispensing devices 900, 1000, and 1100 shown in FIGS. 9, 10, 11, include embodiments of such manual displays. With reference to FIG. 9, a housing 901 defines a window 964. Cover panel 960 may include a fragrance indicator 966. Fragrance indicator 966 may be text, symbols, colors, or any other suitable indicator that identifies the fragrance insert 938 aligned with opening 962. As cover panel 960 rotates so too does fragrance indicator 966. The fragrance indicator 966 associated with fragrance insert 938 aligned with opening 962 is visible through window 964, allowing a user to easily identify which fragrance is being dispense.

With reference to FIG. 10, a housing 1001 defines a window 1064, and fragrance assembly 1036 may include a fragrance indicator 1066. Fragrance indicator 1066 may be text, symbols, colors, or any other suitable indicator that identifies the fragrance insert 1038 aligned with the opening defined in the cover panel (not shown). As fragrance assembly 1036 rotates so too does fragrance indicator 1066. The fragrance indicator 1066 associated with the fragrance insert aligned with an opening of the cover panel (not shown) is visible through window 1064, allowing a user to easily identify which fragrance is being dispensed. User interface 1106 of fragrance dispensing device 1100 in FIG. 11 includes similar features and functions similar to user interface 1006 in FIG. 11, and, thus, like reference numbers are used to generally indicate identical, functionally similar, and/or structurally similar elements.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (for example, a computing device). For example, a machine-readable medium may include read only memory (ROM); random access memory (RAM); magnetic disk storage media; optical storage media; flash memory devices, or the like. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A fragrance dispensing device comprising:
a housing defining an interior cavity, the housing comprising a first portion and a second portion, the second portion being movable relative to the first portion between an open position and a closed position, the first portion of the housing having an intake opening, and the second portion of the housing having a fan mounting area and an exhaust opening;
a fragrance assembly rotatably mounted within the interior cavity of the housing, the fragrance assembly defining a plurality of receptacles for receiving one or more fragrance inserts;
a cover panel configured to substantially seal one or more receptacles of the plurality of receptacles, the cover panel defining an opening;
a fan having an intake and an exhaust, the fan being coupled to the fan mounting area of the second portion of the housing such that the fan moves along with the second portion, wherein the fan is configured to move air from the intake opening of the housing, across the opening in the cover panel, and out the exhaust opening in the housing, thereby releasing a fragrance into an environment.

2. The fragrance dispensing device of claim 1, wherein the intake of the fan is substantially aligned with the opening of the cover panel, and the exhaust of the fan being in fluid communication with the exhaust opening of the housing.

3. The fragrance dispensing device of claim 1, wherein the fan is mounted to an interior surface of the second portion of the housing.

4. The fragrance dispensing device of claim 1, wherein the second portion of the housing is pivotally coupled to the first portion of the housing.

5. The fragrance dispensing device of claim 1, wherein the first portion of the housing comprises a first panel and a second panel extending from the first panel, the second panel defining the intake opening and wherein the fragrance assembly is configured to rotate about an axis perpendicular to the first panel.

6. The fragrance dispensing device of claim 1, wherein the second portion of the housing comprises a panel defining the exhaust opening, and wherein the fan is coupled to the second panel.

7. The fragrance dispensing device of claim 1, further comprising a user interface configured to allow a user to a select a desired fragrance associated with the fragrance inserts received within the receptacles of the fragrance assembly.

8. The fragrance dispensing device of claim 7, wherein the fragrance assembly comprises an RFID tag configured to transmit a signal containing information regarding the fragrance inserts received within the receptacles of the fragrance assembly, and
wherein the fragrance dispensing device further comprises an RFID reader configured to receiver the signal transmitted from the RFID tag.

9. The fragrance dispensing device of claim 1, wherein the fragrance inserts comprise a fragrance infused polymer, and wherein the receptacles have a shape that corresponds to the shape of the fragrance inserts.

10. The fragrance dispensing device of claim 9, wherein the receptacles are sized to create a snap-fit or a press-fit with the fragrance inserts.

11. The fragrance dispensing device of claim 1, further comprising a drive assembly configured to rotate the fragrance assembly such that at least a portion of a user-selected fragrance insert is aligned with the opening of the cover panel.

12. The fragrance dispensing device of claim 11, wherein the drive assembly comprises an electric motor.

13. The fragrance dispensing device of claim 11, wherein the drive assembly comprises a manually operated gear or wheel assembly.

14. A fragrance dispensing device comprising:
a housing defining an interior cavity;
a fragrance disc mounted within the interior cavity of the enclosure, the fragrance disc being configured to rotate about a first axis, the fragrance disc having a periphery with a plurality of teeth, the fragrance disc defining a plurality of receptacles for receiving fragrance inserts; and
a drive assembly comprising a shaft having threads, the drive assembly being configured to selectively rotate the shaft about a second axis, the second axis being substantially perpendicular to the first axis, the drive assembly being positioned such that the threads of the shaft mesh with the teeth of the fragrance disc,
wherein rotation of the shaft about the second axis causes rotation of the fragrance disc about the first axis.

15. The fragrance dispensing device of claim 14, further comprising a cover panel configured to substantially seal one or more receptacles of the plurality of receptacles, the cover panel defining an opening.

16. The fragrance dispensing device of claim 14, wherein the drive assembly is further configured control rotation of the shaft such that at least a portion of a user-selected fragrance insert is aligned with the opening of the cover panel.

17. The fragrance dispensing device of claim 1, wherein at least one of the one or more fragrance inserts comprises:
a main body portion having a first side facing the opening of the cover panel and a second side; and
a plurality of spaced apart ribs extending from the first side of the main body portion,
wherein the main body portion and the plurality of spaced apart ribs comprise a fragrance infused polymer.

18. The fragrance dispensing device of claim 1, wherein the housing defines an opening, and wherein the fragrance assembly is positioned such that a portion of the fragrance assembly extends through the opening of the housing to an exterior of the housing such that a user can selectively rotate the fragrance assembly by contacting the exposed portion of the fragrance assembly.

19. The fragrance dispensing device of claim 1, wherein when the second portion is at the open position, a user has access to the interior cavity defined by the housing, and when the second portion is at the closed position, substantially preventing access to the interior cavity.

20. The fragrance dispensing device of claim 14, wherein the periphery of the fragrance disc is circular.

21. A fragrance dispensing device comprising:
a housing defining an interior cavity, the housing comprising a first portion and a second portion, the second portion being movable relative to the first portion between an open position and a closed position, the first portion of the housing having an intake opening, and the second portion of the housing having a fan mounting area and an exhaust opening;
a fragrance assembly mounted within the interior cavity of the housing, the fragrance assembly defining a plurality of receptacles for receiving one or more fragrance inserts;
a cover panel configured to substantially seal one or more receptacles of the plurality of receptacles, the cover panel defining an opening, the cover panel being rotatably mounted within the interior cavity of the housing, and
a fan having an intake and an exhaust, the fan being coupled to the fan mounting area of the second portion of the housing such that the fan moves along with the second portion,
wherein the fan is configured to move air from the intake opening of the housing, across the opening in the cover panel, and out the exhaust opening in the housing, thereby releasing a fragrance into an environment.

22. The fragrance dispensing device of claim 21, further comprising a drive assembly configured to rotate the cover panel such that at least a portion of a user-elected fragrance insert is aligned with the opening of the cover panel.

* * * * *